United States Patent
Khalfan et al.

(10) Patent No.: US 7,081,594 B1
(45) Date of Patent: Jul. 25, 2006

(54) OPTICAL PAPER SORTING METHOD DEVICE AND APPARATUS

(75) Inventors: Zaheer Khalfan, Scarborough (CA); Sheldon Greenspan, Toronto (CA)

(73) Assignee: Eco-Shred Ltd., Etobicoke (CA)

( * ) Notice: Subject to any disclaimer, the term of this patent is extended or adjusted under 35 U.S.C. 154(b) by 0 days.

(21) Appl. No.: 09/708,038

(22) Filed: Nov. 8, 2000

(30) Foreign Application Priority Data

Oct. 19, 2000 (CA) .............................................. 2323876

(51) Int. Cl.
*B07C 5/342* (2006.01)

(52) U.S. Cl. ...................................... 209/578; 209/587

(58) Field of Classification Search ................. 209/576, 209/577, 578, 587, 639, 938, 939; 256/73, 256/237, 318, 425
See application file for complete search history.

(56) References Cited

U.S. PATENT DOCUMENTS

| | | | | |
|---|---|---|---|---|
| 3,650,400 A | * | 3/1972 | Warren et al. | 250/365 |
| 3,994,602 A | * | 11/1976 | Howarth | 356/208 |
| 4,644,163 A | * | 2/1987 | Selander | 209/577 X |
| 4,715,715 A | * | 12/1987 | Howarth et al. | 356/402 |
| 5,220,172 A | * | 6/1993 | Berthold et al. | 250/461.1 |
| 5,260,584 A | * | 11/1993 | Popson et al. | 205/559.01 |
| 5,398,818 A | * | 3/1995 | McGarvey | 209/639 X |
| 5,640,463 A | * | 6/1997 | Csulits | 382/135 |
| 5,862,919 A | * | 1/1999 | Eason | 209/587 X |
| 5,899,959 A | * | 5/1999 | Shields et al. | 356/237 X |
| 6,052,177 A | * | 4/2000 | Millar et al. | 356/73 |
| 6,335,501 B1 | * | 1/2002 | Khalfan | 209/581 X |
| 6,570,653 B1 | * | 5/2003 | Bruner et al. | 356/417 |
| 2002/0134522 A1 | * | 9/2002 | Karlsson et al. | 162/258 |

* cited by examiner

*Primary Examiner*—Joseph C. Rodriguez
(74) *Attorney, Agent, or Firm*—Dimock Stratton LLP; Mark B. Eisen

(57) ABSTRACT

An optical paper sorting system uses diffuse reflectance to identify a sheet of paper, conveyed on a conveyor, as either white or groundwood grade. A light source illuminates a sheet of paper and an optical collection system collects and filters the light diffusely reflected from the sheet of paper. The reflected light strikes a detector which produces a photoelectric current proportional to the intensity of the filtered light in a specific region in the electromagnetic spectrum, preferably ultraviolet. The signal from the detector may be digitized and processed by a computer which classifies the sheet as either white or groundwood, and activates an ejection device to produce an air blast for diverting whichever grade is selected for ejection.

11 Claims, 4 Drawing Sheets

| WAVELENGTH RANGE (nm) | RELATIVE REFLECTANCE RANGE FOR WHITE COPY PAPER SAMPLES [ % R] | RELATIVE REFLECTANCE RANGE FOR GROUNDWOOD SAMPLES [ % R] |
|---|---|---|
| 200-300 nm | 68-88 % | 15-16 % |
| 300-400 nm | 77-98 % | 18-19 % |
| 200-400 nm | 73-92 % | 16-18 % |

OPTICAL PAPER SORTING METHOD DEVICE AND APPARATUS

FIELD OF THE INVENTION

This invention relates to sorting systems. In particular, this invention relates to an optical materials sorting method, device and apparatus for recyclable materials.

BACKGROUND OF THE INVENTION

Recycling is one of the most environmentally sensible solutions to waste disposal and resource conservation. Many different types of materials can be recycled for reuse, including metals, plastics and paper.

In paper recycling, white copy paper is the most valuable of all recyclable paper grades, while newsprint and file folder stock, which have a high concentration of groundwood, are inferior grades and are considered to be contaminants when found in white copy paper. Thus, during the recycling of high grade white paper, it is desirable that the feed be devoid of high groundwood-content material, which would degrade the finished product. Typically paper sorting is undertaken by workers, who visually identify inferior grades and contaminated white copy paper on a conveyor carrying mixed stock and manually separate inferior grades from the white copy paper.

The separated product inevitably contains an undesirably high content of the inferior grades because visual discrimination is often not very effective, particularly when the conveyor is moving at a high speed. Manual sorting is also undesirable for security reasons, where for example the paper to be recycled contains confidential documents destined for shredding.

Sorting can be done automatically by color detection. However, it is common to encounter groundwood contaminants in the white paper copy paper grade when sorting is based on color, because sensitivity limitations and obscuring of the stock by graphics can result in newsprint and white-colored file folders being graded as white paper.

SUMMARY OF THE INVENTION

The present invention addresses these disadvantages by providing an automatic optical paper sorting method and device which identifies sheets of paper based on the amounts of groundwood they contain. The method and device of the invention is particularly useful for separating sheets of paper containing high amounts of groundwood, such as newsprint and file folders, from sheets of paper containing low levels of groundwood such as standard white copy paper. The method and device can be implemented in a paper sorting apparatus which is advantageously used in the sorting of recyclable paper materials.

In one aspect the invention provides an optical detector which measures the diffuse reflectance, in a specific region of the electromagnetic spectrum, of light incident on a sheet of paper. A light source illuminates the target sheet of paper, and an optical detection system collects a particular spectral component of the diffusely reflected light and generates an electric current proportional to the intensity of the selected spectral component striking the detector. The diffuse reflectance values detected by the device are analyzed to classify the sheets as either groundwood or white.

Preferably, the optical detector comprises a photodetector for receiving the desired spectral component, isolated from the full spectrum of the diffusely reflected light by an optical filter positioned between the photodetector and the target sheet of paper. The isolated spectral component is preferably in the wavelength range 300 to 400 nm, which is the long wave ultraviolet (UV) region of the light spectrum. The device of the invention may alternatively or additionally utilize a light source having an emission spectrum substantially within the desired range.

In the preferred embodiment the device of the invention also provides a data acquisition system which converts the electrical signal into a digital value, and a processor which computes the relative reflectance of the detector output signal by comparing the value of the absolute intensity to a predetermined intensity reference value of a known white sheet of paper.

In a further aspect of the invention a high speed paper sorting apparatus provides the device of the invention mounted over a high speed conveyor belt. In the apparatus the conveyor belt conveys sheets of material to the detection device for identification, and an ejection system ejects sheets identified as falling into the groundwood category.

The present invention thus provides a detection device for differentiating between a material containing less than a selected amount of lignin and a material containing more than the selected amount of lignin, comprising a light source comprising an ultraviolet component positioned to emit light to strike the material, a detector for detecting ultraviolet light and generating an electrical signal proportional to an intensity of detected ultraviolet light, the detector being positioned to detect ultraviolet light diffusely reflected off of the material, an optical filter disposed between the material and the detector to eliminate components of diffusely reflected light outside of the ultraviolet range, and an instrument for measuring a level of the electrical signal, wherein the level of the electrical signal can be compared to a reference level to determine whether the material contains less than or more than the selected amount of lignin.

The present invention further provides a method of differentiating between a material containing less than a selected amount of lignin and a material containing more than the selected amount of lignin, comprising the steps of: a) emitting light comprising an ultraviolet component to strike the material, b) detecting an ultraviolet component of the light diffusely reflected off of the material, c) generating an electrical signal proportional to an intensity of detected ultraviolet light, d) measuring a level of the electrical signal, and e) comparing the level of the electrical signal to a reference level to determine whether the material contains less than or more than the selected amount of lignin.

In further aspects of the device and method of the invention: the material is a paper product; the level of the electrical signal is measured by a computer; the computer compares the level of the electrical signal to a predetermined reference level and outputs a logic high signal or a logic low signal to indicate that the paper product contains more or less than the selected amount of lignin; at least one of the logic high signal or the logic low signal activates a separating mechanism; the light source also emits components outside of the ultraviolet range; and/or the selected amount of lignin is determined by a threshold relative reflectance defined by the equation $$[\% R]_{TS} = [\% R]_{high} \text{ groundwood} + ([\% R]_{low} \text{ white} - [\% R]_{high} \text{ groundwood})/2$$

where $[\% R]_{TS}$ is the threshold relative reflectance, $[\% R]_{high}$ groundwood is an upper limit of groundwood relative reflectance range, and $[\% R]_{low}$ white is a lower limit of white relative reflectance range.

The present invention further provides an apparatus for separating a material containing less than a selected amount of lignin from a material containing more than the selected amount of lignin, comprising a conveyor for conveying the material to a collection bin, a detection device disposed adjacent to the conveyor, comprising a light source positioned to emit light comprising an ultraviolet component to strike the material, a detector for detecting ultraviolet light and generating an electrical signal proportional to an intensity of detected ultraviolet light, the detector being positioned to detect ultraviolet light diffusely reflected off of the material, an optical filter disposed between the material and the detector to eliminate components of diffusely reflected light outside of the ultraviolet range, and an instrument for measuring a level of the electrical signal, a comparing device for comparing the level of the electrical signal to a reference level to determine whether the material contains less than or more than the selected amount of lignin, and an ejection device disposed downstream of the detection device, for receiving an ejection signal from the comparing device when the material contains more than or less than the selected amount of lignin and ejecting the material in response.

In further aspects of the apparatus of the invention: the material is a paper product; the comparing device comprises a computer; the light source also emits components outside of the ultraviolet range; the ejection device comprises an air nozzle receiving air from a compressor; the air nozzle is controlled by a solenoid valve activated by the ejection signal; the air nozzle is disposed adjacent to a terminal end of the conveyor and diverts the material into a rejection bin; and/or the selected amount of lignin is determined by a threshold relative reflectance defined by the equation $$[\% R]_{TS} = [\% R]_{high}\ groundwood + ([\% R]_{low}\ white - [\% R]_{high}\ groundwood)/2$$

where $[\% R]_{TS}$ is the threshold relative reflectance, $[\% R]_{high}$ groundwood is an upper limit of groundwood relative reflectance range, and $[\% R]_{low}$ white is a lower limit of white relative reflectance range.

BRIEF DESCRIPTION OF THE DRAWINGS

In drawings which illustrate by way of example only a preferred embodiment of the invention.

DETAILED DESCRIPTION OF THE INVENTION

Groundwood contains the polymer lignin, which absorbs ultra violet (UV) light. One of the steps in the manufacture of paper is delignification, which involves the removal of lignin from wood pulp. However, the extent of delignification varies depending on the type of paper being manufactured. Paper products such as newsprint and file folders contain substantially higher amounts of lignin compared to regular white copy paper. The higher the lignin content, such as in newsprint, the stronger the absorption in the UV region of the spectrum. Newsprint and other types of paper containing high amounts of groundwood can thus be identified based on the absorption of UV light, which can be determined inferentially by the diffuse reflectance of the paper in the UV range of the spectrum.

When a beam of light impinges on the surface of a sheet of paper, it is either absorbed or diffusely reflected depending on the quality of the paper. The degree of absorption and reflectance varies with the wavelength of the light and the 'whiteness' of the paper. Spectral diffuse reflectance measurements show that regular white copy paper has a substantially higher diffuse reflectance compared to groundwood in the UV region. This difference is due to the lignin content, which has a high affinity for UV light, resulting in a very strong absorbance in the UV region.

Figures 1, 2:
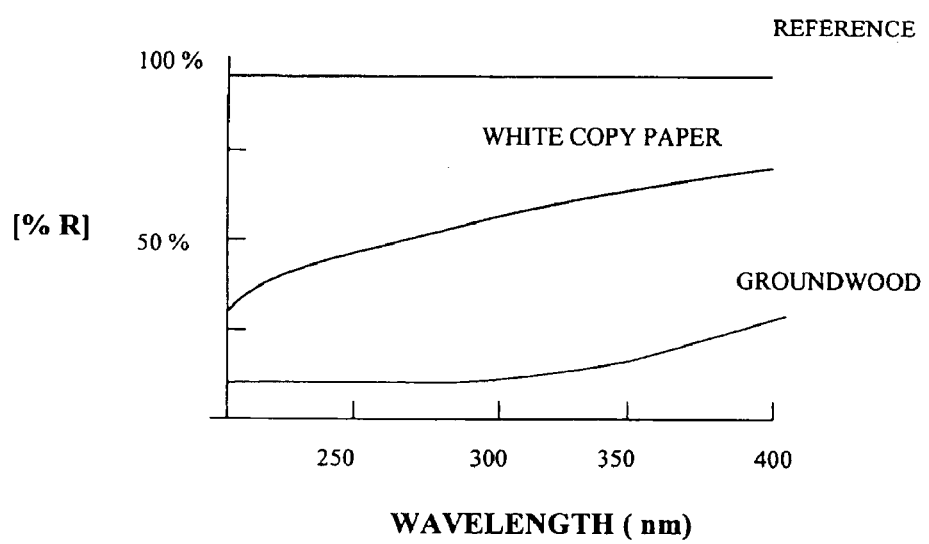
FIG. 1 is a graphical representation of the reflectance of white copy paper and groundwood paper showing reflectivity as a function of wavelength, referenced to a perfect diffuser.
FIG. 2 is a table showing the reflectance ranges of white copy paper and groundwood paper within three selected wavelength ranges.

A perfect diffusing surface reflects all light incident upon it. FIG. 1 shows the percentage reflectance (% R) curves, in the 200–400 nm (UV) wavelength spectral range, for white copy paper, newsprint and a known reference surface having perfect diffusivity. The % R is a relative reflectance, calculated as follows:

$$[\% R] = \frac{\text{Absolute Intensity Of Reflected Light from Sample}}{\text{Absolute Intensity Of Reflected Light from Reference}} \quad (1)$$

In measuring % R the color, intensity and orientation of the incident light beam should be exactly the same for both the samples and the reference. This eliminates the need to measure the intensity of the incident light.

The curves in FIG. 1 illustrate that groundwood exhibits a much lower relative reflectance compared to white copy paper, throughout the 200–400 nm range, referenced to a perfect diffuser.

FIG. 2 shows the relative reflectance range for a white copy paper samples and newsprint samples in the 200–300 nm, 300–400 nm and 200–400 nm ranges of UV light. The relative reflectance values are referenced to a sheet of white copy paper visually selected to be best representative of the desired white grade. Although all UV regions shown exhibit a similar difference in reflectance levels between white copy paper and groundwood, the 300–400 nm range is preferred for safety reasons.

Figure 3:
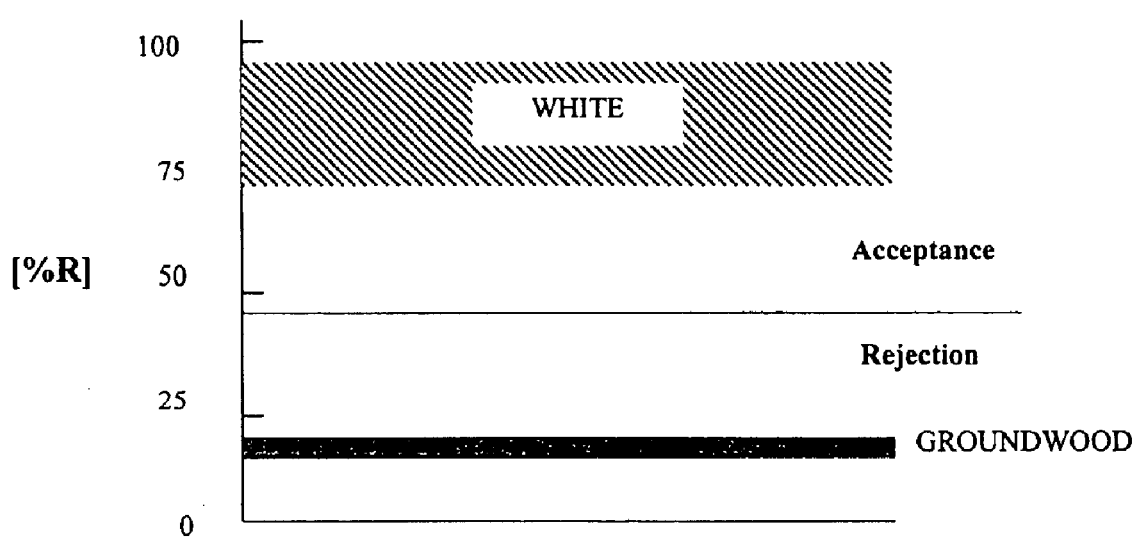
FIG. 3 is a graphical representation of the table of FIG. 2 showing an acceptance-rejection borderline or threshold.

FIG. 3 graphically illustrates the data in the table of FIG. 2, and shows the acceptance-rejection border line which determined by calculating the midpoints of the upper limit of the groundwood relative reflectance range and the lower limit of the white relative reflectance range, as shown below.

$$[\% R]_{TS} = [\% R]_{high}\ groundwood + ([\% R]_{low}\ white - [\% R]_{high}\ groundwood)/2 \quad (2)$$

where $[\% R]_{TS}$ is the Threshold Relative Reflectance, $[\% R]_{high}$ groundwood is the upper limit of groundwood relative reflectance range, and $[\% R]_{low}$ white is the lower limit of white relative reflectance range.

Using formula (2), $[\% R]_{TS}$ has been calculated to be 44% in the 200–300 nm UV light range. The acceptance/rejection algorithm can be expressed as follows;

IF[% R]<[% R]$_{TS}$

SHEET="GROUNDWOOD"

ELSE

SHEET="WHITE"

Figure 5:
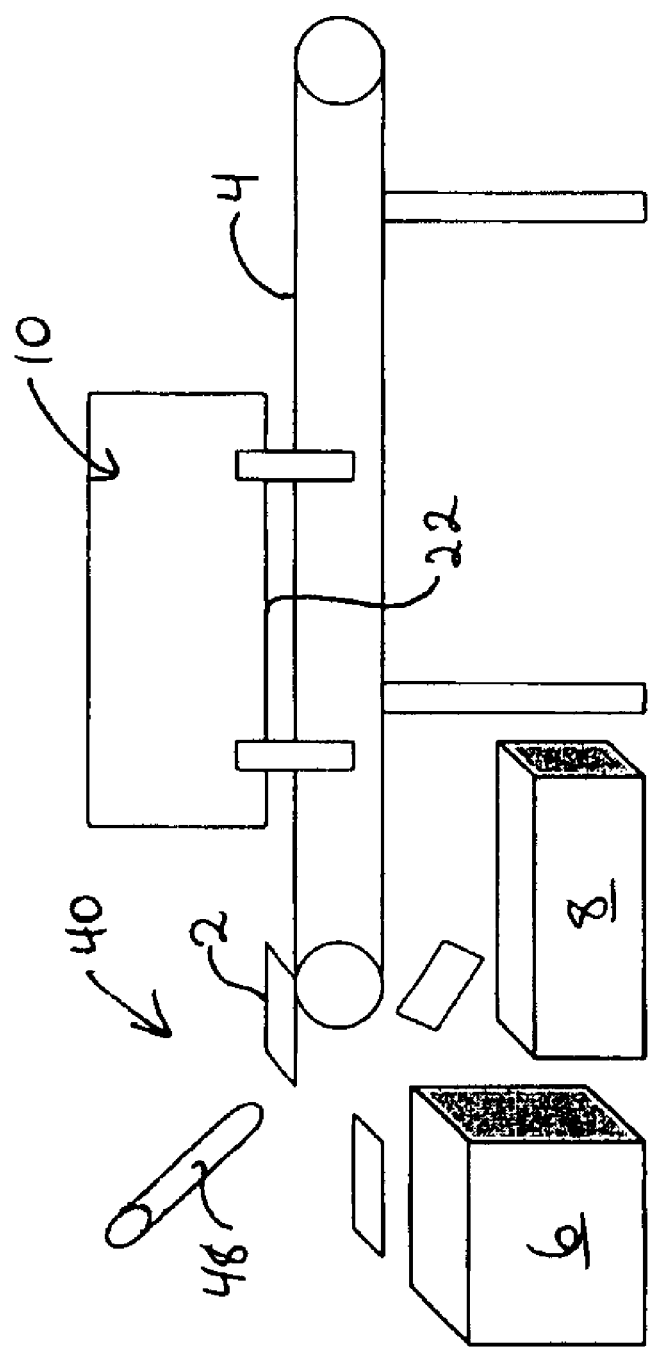
FIG. 5 is a schematic view of a paper separating apparatus according to the invention.

FIG. 5 is a schematic representation of an apparatus according to the present invention. The apparatus comprises a detection device 10 and an ejection system 40.

Figure 4:
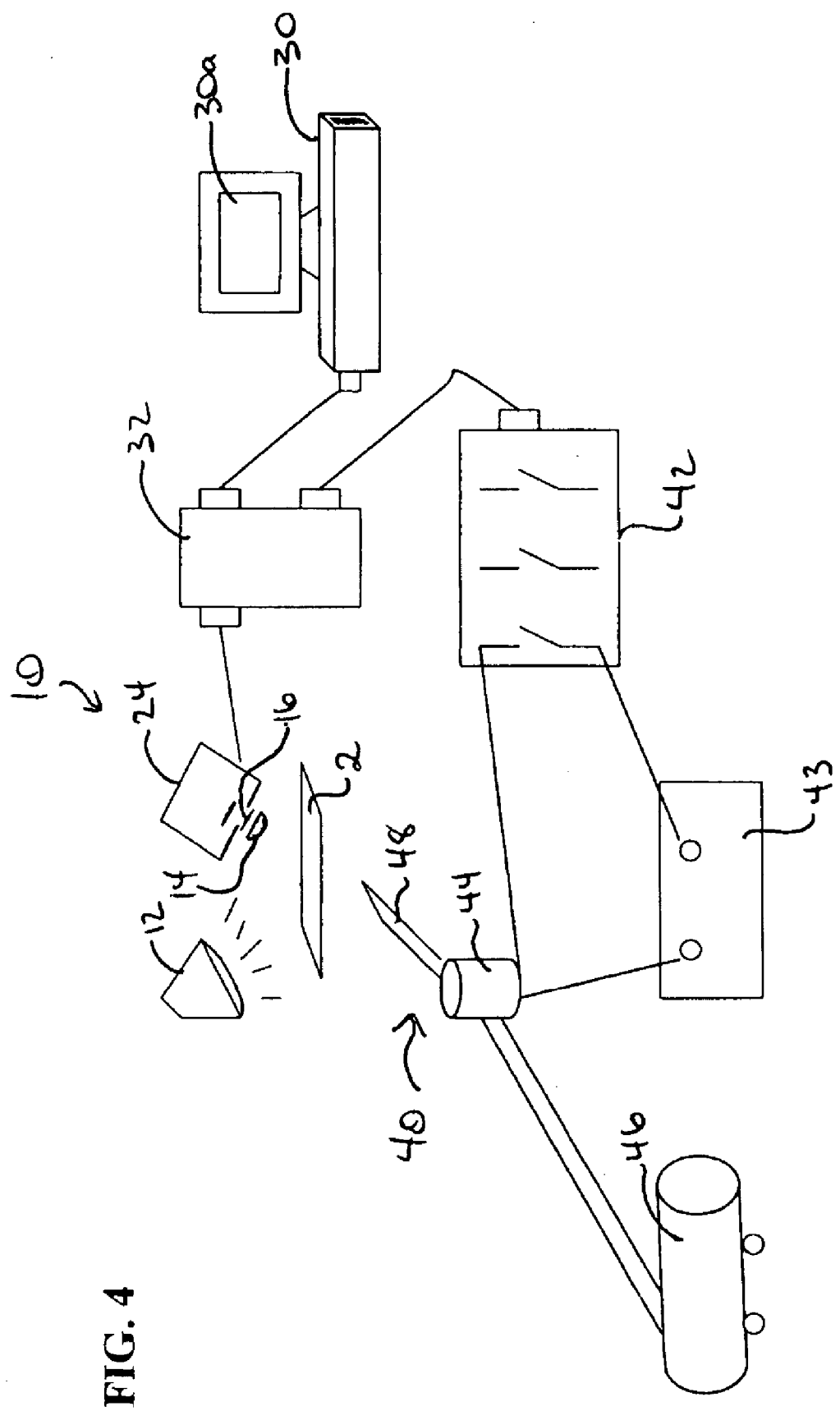
FIG. 4 is a schematic view of a detection device according to the invention.

The detection device 10, illustrated in FIG. 4, includes a light source 12, preferably a mercury vapor light source, which fully illuminates a sheet of paper 2 with a light beam that includes a UV spectral component in the desired range.

In the embodiment shown a plano convex lens 14 collects and collimates the diffusely reflected light. The collimated light is filtered though a UV filter, for example a U-340 Hoya (trademark) filter 16, which isolates the 300–400 nm band. It will thus be appreciated that the light source 12 may be a full spectrum or standard "white" light source which illuminates the sheet 2 in many spectral ranges outside of the UV range, for example visible light regions of the spectrum, because the filter 16 blocks all wavelengths except for those in the selected UV region. Even where the light source 12 is a UV light source confined substantially to the selected UV light region, the filter 16 would be necessary to block light in the visible region of the spectrum produced through fluorescence.

The filter 16 is positioned in front of an aperture 22 through the wall of an opaque detector housing 11 containing a suitable optical detector 24, for example a gallium nitride detector, positioned directly behind the aperture 22. The housing 11 is positioned in a convenient location with the aperture 22 facing the sheet of paper 2. The housing 11 prevents ambient light from striking the detector 24, so that the detector 24 generates a photoelectric current which is directly proportional to the intensity of light diffusely reflected from the paper sheet 2.

In the paper separating apparatus of the invention the detection device 10 is disposed adjacent to the conveyor 4 such that incident light emitted from the light source 12 and diffusely reflected off of the paper sheet 2 traverses the aperture 22 and strikes the detector 24. In the embodiment shown the sheets 2 are supported on top of the conveyor 4 by gravity, and the device 10 is thus positioned above the conveyor 4. In other embodiments, where for example the sheets 2 are retained on the conveyor 4 by air suction or other mechanical means, the conveyor 4 may be oriented in any fashion and the detection device 10 would be positioned accordingly, so that incident light from the light source 12 reflects off of the sheet 2 and enters the aperture 22 of the detector housing 11.

The level of the electrical signal generated by the detector 24 may be measured by any suitable instrument and manually compared against a reference level. However, the preferred embodiment of the invention is automatic and includes a data processing device, such as a personal computer or microcomputer 30, which processes the reflectance values generated by the detector 24 and operates the ejection system 40 in the paper separating apparatus. The photoelectric current generated by the detector 24 is carried by a suitable connection to an analog input port of an analog to digital converter 32, which digitizes the signal and outputs the digital equivalent signal to the computer 30, for example through a parallel connection. The computer 30 is programmed to receive data representative of the intensity of each signal, calculate the relative reflectance of the sheet 2 and apply the algorithm set out above to determine whether the sheet 2 is classified as 'white' or 'groundwood'.

Preferably the computer 30 is also programmed to display the absolute value of digitized signal, the computed value of % R and the type of paper ('white' or 'groundwood') on a monitor 30a. The computer 30 is further programmed to output either a high or low logic signal depending on which of the two classes of sheets (white or groundwood) has been detected, the high logic signal being an ejection signal which activates the ejection system 40. Preferably, because groundwood normally occurs in smaller quantities in the mixed stock, groundwood is selected as the grade to be ejected.

Thus, when the output from the computer 30 is low, no ejection signal is generated; when the computer 30 determines that a sheet of paper 2 falls into the 'groundwood' class, it outputs an ejection signal. In the embodiment shown the ejection signal is transmitted back to the AD converter 32 over the parallel cable connection with the computer 30, and the AD converter 32 in turn sends a digital output signal to the relay switch 42 to activate the ejection system 40. Alternatively, the ejection signal may be transmitted directly to a relay card associated with the relay switch 42 to activate the ejection system 40.

The ejection system 40 releases a momentary blast of air to divert a sheet 2 of groundwood paper from the primary collection bin 6 to a rejection bin 8. The bins 6, 8 are thus positioned adjacent to the end of a conveyor 4 such that a sheet 2 reaching the end of the conveyor 4 will fall into the primary collection bin 6 unless diverted to the rejection bin 8, as shown in FIG. 5. The conveyor 4 should preferably be black or dark-colored, to reduce opportunities for light reflecting off of the conveyor 4 to enter the aperture 22 and strike the detector 24.

The ejection system 40 comprises relay switch 42, one terminal of which is connected to a two-way normally closed solenoid valve 44 and the other terminal of which is connected to one terminal of a power supply, for example a conventional 120 V mains power supply 43. The other terminal of the power supply is connected to the solenoid valve 44 to form a circuit through the relay switch 42, solenoid valve 44 and power supply. A compressor 46 is in communication with an air nozzle 48 connected to the outlet port of the solenoid valve 44 and directed at the terminal end of the conveyor 42, to divert a rejected sheet of paper 2 into the rejection bin 8.

In operation, the conveyor 4 is activated and sheets 2 of paper are fed onto the conveyor 4 upstream of the detector housing 20, either manually or by any suitable mechanical feeding means (not shown). The conveyor 4 conveys the sheets 2, one at a time, past the detector housing 20. As each sheet 2 passes the housing 20 light from the light source 12, collimated by the lens 14, strikes the sheet 2 and reflects through the filter 16 into the aperture 22, striking the detector 24. The detector 24 generates an analog electrical signal proportional to the intensity of light striking the detector, which signal is digitized by AD converter 32 and output to the computer 30.

The computer 30, having been programmed with the appropriate algorithms and a reference level, calculates the percent reflectance of the sheet 2 and compares the % R value to the preprogrammed acceptance-rejection threshold. If the calculated % R is above the acceptance-rejection threshold, the computer 30 outputs a logic low signal (or no signal) and the sheet 2 is conveyed to the terminal end of the conveyor 4 where it falls into the primary collection bin 6.

If the calculated % R is above the acceptance-rejection threshold, the computer 30 outputs a logic high signal to activate the ejection system 40. When the relay switch 42 receives the high input signal from the computer 30, the relay switch 42 closes and completes the circuit, causing a current to pass through the solenoid valve 44, which in turn opens to release a blast of air from the compressor 46 through the air nozzle 48. The distance between the air nozzle 48 and detection device 10, along with the speed of the conveyor 4, determines the time lapse between detection and ejection. The relay switch 42 may be activated after a suitable delay interval, to account for the time taken between detection of the % R from the sheet 2 and conveyance of the sheet to the terminal end of the conveyor 4, however with the conveyor 4 set to a high enough speed and the detection device 10 suitably positioned near the terminal end of the conveyor 4, a delay may be unnecessary.

The air blast causes the sheet of paper 2 to be diverted into the rejection bin 8, which may for example be positioned beneath the terminal end of the conveyor 4, as shown in FIG. 5. The air nozzle 48 is thus mounted beyond the terminal end of the conveyor 4 in such a way that the air nozzle is directed towards the terminal end of the conveyor 4. The undiverted 'white' grade sheets 2 fall into the primary collection bin 6 positioned adjacent to the terminal end of the conveyor 4 under the influence of gravity. It will be appreciated that the ejection system 40 can be positioned anywhere downstream of the detection device 10, and the embodiment illustrated is merely a preferred embodiment. It will also be appreciated that the 'white' sheets 2 could also be mechanically (pneumatically or otherwise) diverted into the primary collection bin 6, which would allow greater flexibility in the positioning of the bin 6 but would increase the cost of the apparatus.

In the preferred embodiment the duration of the air blast is equal to the length of time the sheet of paper is "viewed" by the detection device 10. The computer. 30 can be programmed to time the interval between the start and end of a reflectance signal from the AD converter 32, which respectively correspond to the sheet 2 entering and leaving the view field of the detector 24, and to maintain the high output signal for this interval in order to ensure that the sheet 2 is properly diverted into the rejection bin 8.

It will be appreciated that the device and apparatus of the present invention can be adopted to sort and separate other fibrous objects or objects containing lignin fiber besides paper, utilizing the principles of the invention to differentiate between lignin levels in two or more categories. The invention may also be used to sort and separate paper into more than two categories, by defining a plurality of classification thresholds, increasing the logic output options (for example by outputting to the ejection device a multiple-bit word rather than a high or low signal), and providing a sufficient number ejection systems (i.e. at least one less than the number of classifications) to separate materials of the different classes.

A preferred embodiment of the invention having been thus described by way of example only, it will be apparent to those skilled in the art that certain modifications and adaptations may be made without departing from the scope of the invention, as set out in the appended claims.

We claim:

1. A detection device for differentiating between a paper product containing less than a selected amount of lignin and a paper product containing more than the selected amount of lignin, the paper products being of the same color or of a different color, comprising a light source comprising an ultraviolet component positioned to emit light to strike the paper product, a detector for detecting ultraviolet light and generating an electrical signal proportional to an intensity of detected ultraviolet light, the detector being positioned to detect ultraviolet light diffusely reflected off of the paper product, an optical filter disposed between the paper product and the detector to eliminate components of diffusely reflected light outside of the ultraviolet range, and an instrument comprising a computer programmed to compare the level of the electrical signal to a predetermined reference level and to output a logic high signal or a logic low signal to indicate that the paper product contains more or less than the selected amount of lignin, for measuring a level of the electrical signal, wherein the level of the electrical is compared to a reference level to determine whether the paper product contains less than or more than the selected amount of lignin.

2. The device as defined in claim 1 in which at least one of the logic high signal or the logic low signal activates a separating mechanism.

3. The device as defined in claim 1 in which the light source also emits light components outside of the ultraviolet range.

4. The device as defined in claim 1 in which the selected amount of lignin is determined by a threshold relative reflectance defined by the equation $$[\% R]_{TS} = [\% R]_{high} \text{ groundwood} + ([\% R]_{low} \text{ white} - [\% R]_{high} \text{ groundwood})/2$$

where $[\% R]_{TS}$ is the threshold relative reflectance, $[\% R]_{high}$ groundwood is an upper limit of groundwood relative reflectance range, and $[\% R]_{low}$ white is a lower limit of white relative reflectance range.

5. A method or differentiating between a material containing less than a selected amount of lignin and a material containing more than the selected amount of lignin, the materials being of the same color or of a different color, comprising the steps of:

a) emitting light comprising an ultraviolet component to strike the material, b) detecting an ultraviolet component of the light diffusely reflected off of the material, c) generating an electrical signal proportional to an intensity of detected ultraviolet light, d) measuring a level of the electrical signal, and e) comparing the level of the electrical signal to a reference level to determine whether the material contains less than or more than the selected amount of lignin.

6. The method as defined in claim 5 in which the material is a paper product.

7. The method as defined in claim 6 in which the level of the electrical signal is measured by a computer.

8. The method as defined in claim 7 in which the computer compares the level of the electrical signal to a predetermined reference level and outputs a logic high signal or a logic low signal to indicate that the paper product contains more or less than the selected amount of lignin.

9. The method as defined in claim 8 in which at least one of the logic high signal or the logic low signal activates a separating mechanism.

10. The method as defined in claim 6 in which the selected amount of lignin is determined by a threshold relative reflectance defined by the equation $$[\% R]_{TS} = [\% R]_{high} \text{ groundwood} + ([\% R]_{low} \text{ white} - [\% R]_{high} \text{ groundwood})/2$$

where $[\% R]_{TS}$ is the threshold relative reflectance, $[\% R]_{high}$ groundwood is an upper limit of groundwood relative reflectance range, and $[\% R]_{low}$ white is a lower limit of white relative reflectance range.

11. The method as defined in claim 5 wherein the emitted light includes components outside of the ultraviolet range.

* * * * *